(12) United States Patent
Kunath et al.

(10) Patent No.: US 7,861,356 B2
(45) Date of Patent: Jan. 4, 2011

(54) BRUSH HEAD FOR ELECTRIC AND/OR MANUAL TOOTHBRUSHES

(75) Inventors: Ivo Kunath, Kronberg (DE); Georges Driesen, Weilrod (DE); Thomas Fritsch, Eppstein (DE); Armin Schwarz-Hartmann, Wendelsheim (DE)

(73) Assignee: Braun, GmbH, Kronberg (DE)

( * ) Notice: Subject to any disclaimer, the term of this patent is extended or adjusted under 35 U.S.C. 154(b) by 878 days.

(21) Appl. No.: 11/569,789

(22) PCT Filed: May 21, 2005

(86) PCT No.: PCT/EP2005/005538

§ 371 (c)(1),
(2), (4) Date: Nov. 29, 2006

(87) PCT Pub. No.: WO2005/115196

PCT Pub. Date: Dec. 8, 2005

(65) Prior Publication Data

US 2007/0256263 A1    Nov. 8, 2007

(30) Foreign Application Priority Data

May 29, 2004   (DE) ................. 10 2004 026 461

(51) Int. Cl.
*A46B 7/02* (2006.01)
(52) U.S. Cl. .............. 15/110; 15/22.1; 15/28; 15/167.1; 15/188; 601/141; 601/142
(58) Field of Classification Search .......... 15/110, 15/114, 117, 121, 22.1, 28, 167.1, 188; 601/141, 601/142
See application file for complete search history.

(56) References Cited

U.S. PATENT DOCUMENTS

| 1,268,544 | A |   | 6/1918  | Cates |
|-----------|---|---|---------|-------|
| 1,935,417 | A |   | 11/1933 | Robinson |
| 2,088,839 | A | * | 8/1937  | Coney et al. ............ 15/167.1 |
| 2,139,245 | A |   | 12/1938 | Ogden |
| 2,189,175 | A | * | 2/1940  | Jackson ................ 601/141 |
| 2,364,205 | A |   | 12/1944 | Fuller |
| 2,789,352 | A |   | 4/1957  | Wiseman |
| 3,196,299 | A | * | 7/1965  | Kott ..................... 310/81 |

(Continued)

FOREIGN PATENT DOCUMENTS

DE    1 922 022    8/1968

(Continued)

OTHER PUBLICATIONS

Examiner's Answer for U.S. Appl. No. 10/364,148 dated May 19, 2008; Braun; filed Feb. 11, 2003.
Office Action for U.S. Appl. No. 10/364,148 dated Dec. 21, 2007; Braun; filed Feb. 11, 2003.
Office Action for U.S. Appl. No. 10/364,148 dated Jul. 6, 2007; Braun; filed Feb. 11, 2003.

(Continued)

*Primary Examiner*—Mark Spisich
(74) *Attorney, Agent, or Firm*—George H. Leal

(57) ABSTRACT

A brush head of compact design, which includes a bristle carrier having secured to it bristles, and an elastic element for holding an oral, dental and/or gingival cleaning and/or care substance. The elastic element is joined to the bristle carrier by means of a support element. The bristle carrier is made of a first plastic, the support element of a second plastic, and the elastic element of a third plastic.

15 Claims, 5 Drawing Sheets

U.S. PATENT DOCUMENTS

| | | | |
|---|---|---|---|
| 4,538,631 A | 9/1985 | Prince | |
| 4,929,180 A | 5/1990 | Moreschini | |
| 5,058,230 A * | 10/1991 | Hodosh et al. | 15/167.1 |
| 5,360,339 A | 11/1994 | Rosenberg | |
| 5,378,153 A | 1/1995 | Giuliani et al. | |
| 5,584,690 A | 12/1996 | Maassarani | |
| D378,166 S | 2/1997 | Savitt et al. | |
| 5,604,951 A | 2/1997 | Shipp | |
| 5,735,011 A | 4/1998 | Asher | |
| 5,930,860 A | 8/1999 | Shipp | |
| 6,146,140 A | 11/2000 | Bailey | |
| 6,237,178 B1 | 5/2001 | Krammer et al. | |
| 6,347,425 B1 * | 2/2002 | Fattori et al. | 15/22.1 |
| 6,374,448 B2 | 4/2002 | Seifert | |
| 6,490,747 B1 | 12/2002 | Metwally | |
| 6,513,182 B1 | 2/2003 | Calabrese et al. | |
| 6,553,604 B1 * | 4/2003 | Braun et al. | 15/167.1 |
| D476,157 S | 6/2003 | Gatzemeyer et al. | |
| 6,571,417 B1 | 6/2003 | Gavney, Jr. et al. | |
| 6,665,901 B2 | 12/2003 | Driesen et al. | |
| 6,766,548 B1 | 7/2004 | Lukas et al. | |
| 6,993,804 B1 * | 2/2006 | Braun et al. | 15/110 |
| 7,174,596 B2 | 2/2007 | Fischer et al. | |
| 7,181,799 B2 | 2/2007 | Gavney et al. | |
| 7,392,562 B2 | 7/2008 | Boland et al. | |
| 2001/0023516 A1 | 9/2001 | Driesen et al. | |
| 2003/0033680 A1 | 2/2003 | Davies et al. | |
| 2003/0159224 A1 | 8/2003 | Fischer et al. | |
| 2003/0229959 A1 | 12/2003 | Gavney, Jr. et al. | |
| 2004/0060135 A1 | 4/2004 | Gatzemeyer et al. | |
| 2004/0154112 A1 | 8/2004 | Braun | |
| 2004/0177462 A1 * | 9/2004 | Brown et al. | 15/167.1 |
| 2009/0282628 A1 | 11/2009 | Braun | |

FOREIGN PATENT DOCUMENTS

| | | |
|---|---|---|
| DE | 25 26 893 | 12/1976 |
| DE | 43 03 431 | 8/1993 |
| DE | 197 17 868 | 10/1998 |
| DE | 201 11 428 | 1/2003 |
| DE | 101 64 336 | 7/2003 |
| FR | 936 529 | 7/1948 |

OTHER PUBLICATIONS

Advisory Action for U.S. Appl. No. 10/364,148 dated May 7, 2007; Braun; filed Feb. 11, 2003.

Office Action for U.S. Appl. No. 10/364,148 dated Dec. 21, 2006; Braun; filed Feb. 11, 2003.

Office Action for U.S. Appl. No. 10/364,148 dated May 12, 2006; Braun; filed Feb. 11, 2003.

Office Action for U.S. Appl. No. 10/364,148 dated Nov. 14, 2005; Braun; filed Feb. 11, 2003.

Office Action for U.S. Appl. No. 10/364,148 dated May 5, 2005; Braun; filed Feb. 11, 2003.

Office Action for U.S. Appl. No. 10/364,148 dated Dec. 16, 2004; Braun; filed Feb. 11, 2003.

Office Action for U.S. Appl. No. 10/364,148 dated Jul. 14, 2004; Braun; filed Feb. 11, 2003.

Office Action for U.S. Appl. No. 12/483,838 dated Feb. 18, 2010; Braun; filed Jun. 12, 2009.

Office Action for U.S. Appl. No. 12/483,838 dated Aug. 2, 2010; Braun; filed Jun. 12, 2009.

* cited by examiner

BRUSH HEAD FOR ELECTRIC AND/OR MANUAL TOOTHBRUSHES

TECHNICAL FIELD

This invention relates to a brush head having a bristle carrier on which bristles and an elastic element are fixed.

BACKGROUND

FR936 529 describes an electric toothbrush with a bristle head comprising bristles and a container for a gingival fortification substance.

DE 101 64 336 describes a toothbrush with a handle and a head part on which is arranged a soft elastic cleaning element that is mounted on the head part by way of a carrier element. The carrier element and the head part are made from the same plastic.

SUMMARY

One aspect of the present invention is a brush head having an elastic element joined to a bristle carrier in such a way as to enable a compact design. In some embodiments, the elastic element is joined to the bristle carrier by means of a support element, whereby the bristle carrier is made of a first plastic with high wear resistance, high impact strength, high mechanical strength, high dimensional stability and resistance to chemicals, for example polyoxymethylene (POM). The support element is made of a second plastic, for example polypropylene (PP). The elastic element is made of a third plastic, for example a thermoplastic elastomer (TPE).

This selection of materials provides a material for the elastic element that is gentle on the gums and teeth, i.e., a relatively soft material. Elastic materials with a relatively low Shore hardness can also be used. However, such very soft materials cannot be joined permanently in a positive-engagement relationship to a bristle carrier made of polyoxymethylene, but only to a bristle carrier made of polypropylene. This material is unsuitable for bristle carriers, in particular in cases where an oscillating brush head is used. The excessively low impact strength reduces the pull-out forces of the bristles. As a result, the bristle depth needs to be significantly increased, and this substantially increases the thickness of the bristle carrier.

In some embodiments, the support element, which joins the elastic element to the bristle carrier, is made of polypropylene. A support element made from this plastic can easily be fixed to a bristle carrier made from polyoxymethylene, and it can also be joined effectively and permanently, by bonding of the materials involved, to an element made from a soft elastic plastic, for example, a thermoplastic polymer. Compared to a joint produced by positive engagement, a joint obtained by material bonding accommodates a compact design. In some embodiments, the support element is fixed centrally in the brush head underneath the elastic element.

In some embodiments, the bristle carrier has a brush disk, having an oval or round shape, with tufts of bristles being mounted on the bristle carrier and arranged around an elastic container that is used to hold an oral, dental and/or gingival cleaning and/or care substance. This approach results in a good application of a dental care substance, for example a teeth whitening agent. Also, this approach results in a good cleaning effect by the bristles, for example in the use of a bristle carrier performing an oscillatory rotational motion. The elastic container is open to a tooth-cleaning side in order to receive the cleaning and/or care substance.

Conveniently, the support element is arranged centrally in a depression on a bristled side of the bristle carrier, whereby the support element serves an anchoring function for the elastic container. This results in a very compact design of the brush head, which is hardly larger than a standard brush head.

The support element can be joined to the bristle carrier in a variety of ways, for example, by positive engagement using through-holes on the bristle carrier, or by clipping the support element into the bristle carrier, or by material bonding, such as by ultrasonic welding.

In some embodiments, the elastic container is joined to the support element by material bonding. The container can have a central depression on its undersurface, and a corresponding elevation can be formed on the support element, as these shapes increase the joining area between the two parts, thus enhancing interface adhesion between the materials. The depression can be constructed in the form of a truncated cone.

The bristle carrier can be equipped with different types of bristle tuft, which differ in their number of bristles and/or arrangement of bristles and/or geometry (according to the depressions in the bristle carrier for fastening the bristle tufts), and whose bristles differ in their length, diameter, hardness and/or material.

The present invention and its advantages will be explained in the following with reference to embodiments of brush heads illustrated in the Figures of the accompanying drawing.

DETAILED DESCRIPTION

Figure 1:
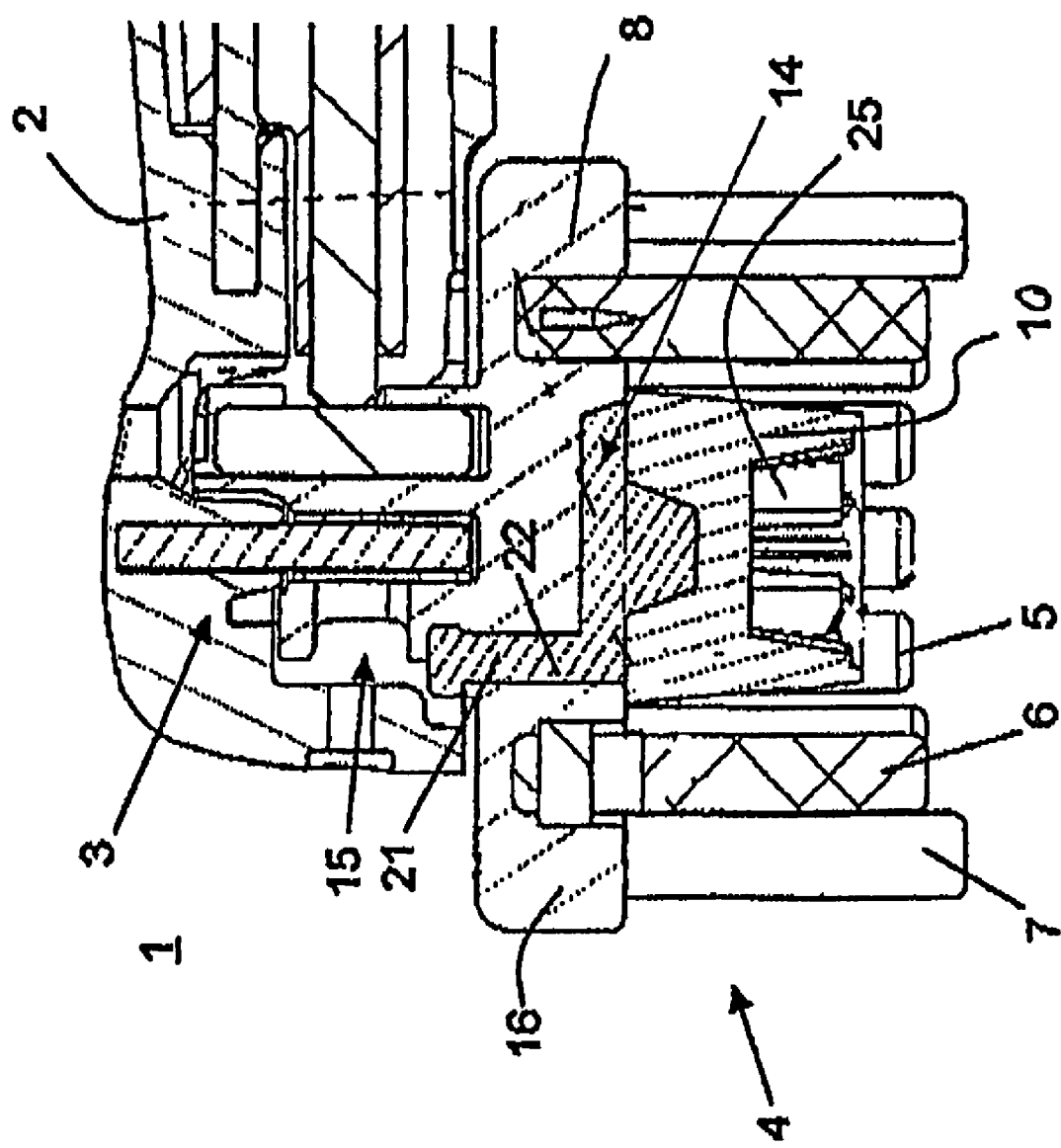
FIG. 1 is a sectional view of a brush attachment with a brush head.

The brush attachment 1 shown in FIG. 1 has a brush shank 2 and a drive mechanism 3 for transmitting an oscillatory rotational drive motion to a brush head 4. The brush head mounts a bristle carrier 8, which carries bristles 5 to 7, or bristle tufts, and in which the tufts are fastened in depressions. Arranged inside a bristled area is an elastic element 10 in the form of a container which serves to hold oral care substances such as toothpaste or agents for whitening teeth.

The bristle carrier 8 is made from a wear-resistant material, for example polyoxymethylene, and includes a bearing arrangement 15 in the brush head 4. With this selection of material the bearing arrangement 15 continues to be functional even after prolonged use of the brush head 4. The brush shank 2 can also be made from polyoxymethylene. The thickness of a brush disk 16 of the bristle carrier 8 is relatively small, for example in the range of 2.5 mm to 3.5 mm, in particular around 3 mm. The bristles 5 to 7 are embedded to a depth of around 2 mm in the brush disk 16, which is sufficient given this selection of material.

A support element 14 can be made of polypropylene. The container 10 is made of a thermoplastic elastomer, and is joined to the support element 14 by material bonding.

Figure 2:
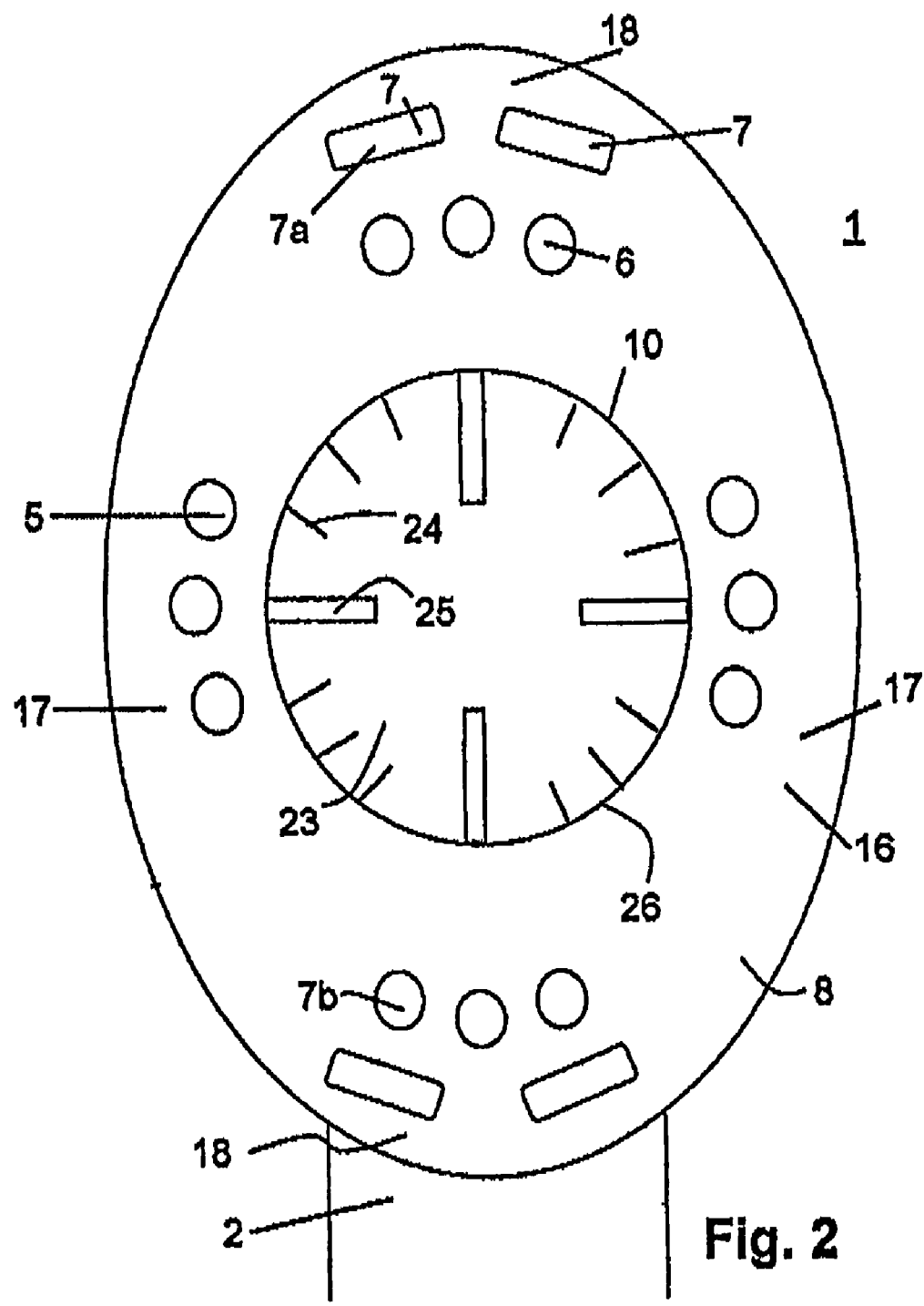
FIG. 2 is a schematic view of a brush head as seen looking from the bristle side.

As becomes apparent from FIG. 2, the bristle carrier 8 has an oval shape. A round or other shape is also possible. The bristle tufts 5-7 are fastened to the bristle carrier 8 and arranged around the elastic container 10. The bristles may project to a greater or lesser extent beyond the elastic container 10, cf. FIG. 1. The bristles or bristle tufts 5 arranged in regions 17 of the smaller semiaxis of the oval are relatively short, with the tufts having a round cross section. The bristle tufts arranged in regions 18 of the larger semiaxis have either a round 6 or elongated 7 cross section. The bristles 7a located farther away from the brush shank 2 can be somewhat longer than the bristles 7b close to the shank.

The bristle carrier 8 can also be equipped with different types of bristles which differ in their length, diameter, hardness and/or material. The bristle tufts can differ in number and/or arrangement of their bristles and/or geometry.

FIG. 1 shows that the support element 14 for the elastic container 10 is embedded centrally in a depression 20 on a bristled side of the bristle carrier 8. The support element 14 is joined to the bristle carrier 8 by connecting fingers 22 making positive engagement with corresponding through-holes 21 in the bristle carrier. The end of the connecting finger 22 has a larger cross section causing the two parts to be securely joined together. Other positive-engagement joints, or a positive-frictional engagement joint, or a clip-in joint are also possible.

The elastic container 10 is open to the tooth-cleaning side and serves to hold an oral, or dental, or gingival care substance, or a teeth whitening agent. For better adhesion of the agent to the elastic container 10, inwardly extending ribs 24, 25 are integrally formed on an outer wall 26 (outer wall 26 is round as shown in FIG. 2, but other shapes may be used) of the elastic container 10. For example, provision is made for four long ribs 25 in a crosshair-type arrangement and for twelve short ribs 24.

The elastic container 10 has a central depression on its undersurface. A corresponding elevation is formed on the support element 14. The depression is constructed in the form of a truncated cone.

Figure 3:
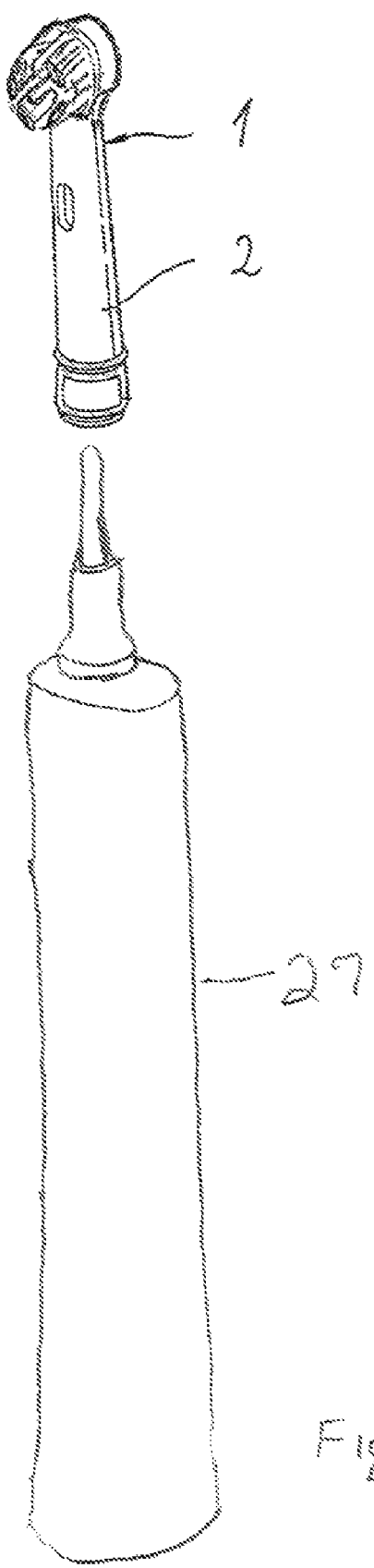
FIG. 3 is a view of an electric toothbrush with the brush head.
Figure 4:
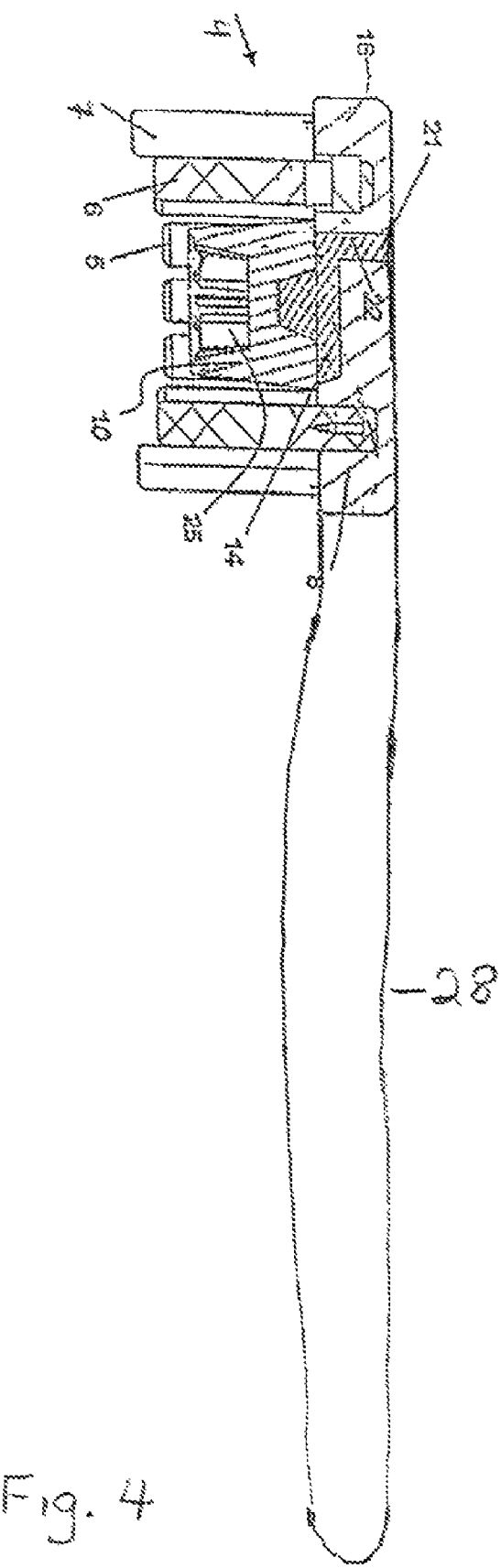
FIG. 4 is a view of a manual toothbrush with the brush head.
Figure 5:
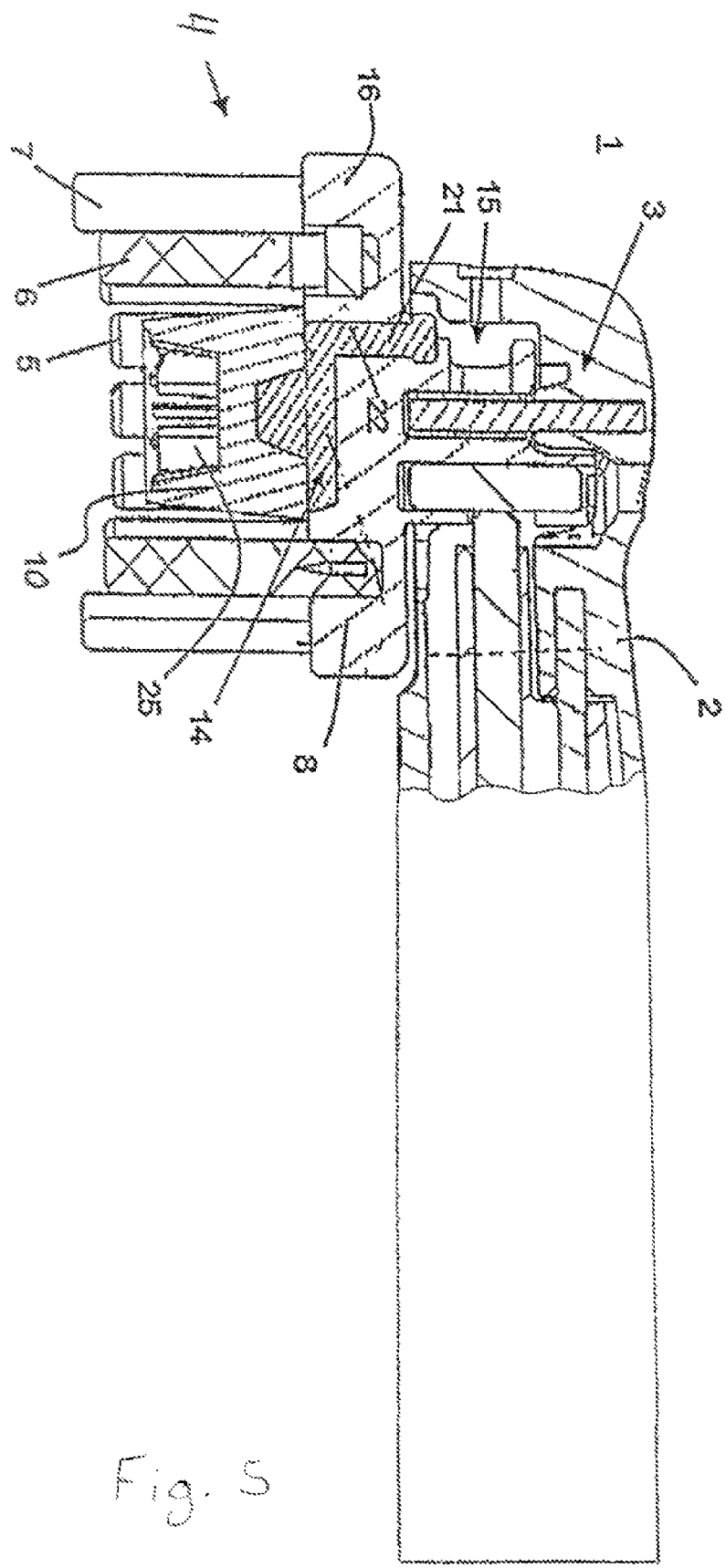
FIG. 5 is another sectional view of the brush attachment with the brush head.

Referring to FIG. 3, the described brush head is shown in brush attachment 1 (shown additionally in FIG. 5) which is designed to be fitted on an electric toothbrush 27. The described brush head can also be used on a manual toothbrush 28 shown in FIG. 4.

It should be understood that the present invention is not limited to only the embodiments presented. It also covers embodiments similar in effect within the meaning of the teaching of the description. For example, comparable materials can be used, or provision made for a different configuration of the brush head or the elastic element. For example, the elastic element can also be constructed as a rod-shaped massage element.

Other embodiments are within the scope of the following claims.

The invention claimed is:

1. A brush head for a toothbrush comprising:
a bristle carrier on which bristles are fixed;
an elastic element fixed on the bristle carrier, the elastic element being joined to the bristle carrier by a support element, wherein the bristle carrier is made of a first plastic, the support element is made of a second plastic, and the elastic element is made of a third plastic, wherein the elastic element is constructed as a container designed to hold one or more of an oral, dental or gingival cleaning or care substance, said container being open to a tooth-cleaning side, and wherein the container is provided with ribs on an inside of a wall.

2. The brush head according to claim 1, wherein the bristle carrier is made of polyoxymethylene.

3. The brush head according to claim 1, wherein the support element is made of polypropylene.

4. The brush head according to claim 1, wherein the elastic element is made of a thermoplastic elastomer.

5. The brush head according to claim 4, wherein the elastic element is joined to the support element by bonding of the materials involved.

6. The brush head according to claim 1, wherein the support element is joined to the bristle carrier by positive engagement.

7. The brush head according to claim 6, wherein the support element is joined to the bristle carrier by connecting fingers engaging in corresponding through-holes in the bristle carrier.

8. The brush head according to claim 1, wherein the ribs are of different length.

9. The brush head according to claim 1, wherein the bristle carrier includes different types of bristle tufts which differ in one or more of their number of bristles, arrangement of bristles, and geometry, and whose bristles differ in one or more of their length, diameter, hardness, and material.

10. An electric toothbrush having a brush head according to claim 1.

11. A manual toothbrush having a brush head according to claim 1.

12. A brush attachment for an electric and/or manual toothbrush having a brush head according to claim 1.

13. The brush head according to claim 1, wherein the support element is joined to the bristle carrier by a clip-in joint.

14. The brush head according to claim 1, wherein the support element is joined to the bristle carrier by frictional engagement.

15. The brush head according to claim 1, wherein the support element is joined to the bristle carrier by frictional and positive engagement.

* * * * *